(12) United States Patent
Silver

(10) Patent No.: US 11,339,125 B2
(45) Date of Patent: *May 24, 2022

(54) USE OF ISOTHIOCYANATE FUNCTIONAL SURFACTANTS AS NRF2 INDUCERS TO TREAT EPIDERMOLYSIS BULLOSA SIMPLEX AND RELATED DISEASES

(71) Applicant: Michael E. Silver, Lake City, MI (US)

(72) Inventor: Michael E. Silver, Lake City, MI (US)

(73) Assignee: The William M. Yarbrough Foundation, Peoria, IL (US)

( * ) Notice: Subject to any disclaimer, the term of this patent is extended or adjusted under 35 U.S.C. 154(b) by 6 days.

This patent is subject to a terminal disclaimer.

(21) Appl. No.: 16/867,538

(22) Filed: May 5, 2020

(65) Prior Publication Data

US 2021/0017130 A1     Jan. 21, 2021

Related U.S. Application Data

(63) Continuation of application No. 16/506,119, filed on Jul. 9, 2019, now Pat. No. 10,640,464, which is a continuation of application No. 16/218,711, filed on Dec. 13, 2018, now Pat. No. 10,343,990, which is a continuation-in-part of application No. 15/675,915, filed on Aug. 14, 2017, now abandoned, which is a continuation-in-part of application No. 15/353,260, filed on Nov. 16, 2016, now Pat. No. 9,962,361, which is a continuation-in-part of application No. 15/297,304, filed on Oct. 19, 2016, now Pat. No. 9,951,005, which is a continuation of application No. 14/594,788, filed on Jan. 12, 2015, now Pat. No. 9,951,003, which is a continuation of application No. 13/342,516, filed on Jan. 3, 2012, now Pat. No. 8,933,119.

(60) Provisional application No. 61/502,067, filed on Jun. 28, 2011, provisional application No. 61/429,325, filed on Jan. 3, 2011.

(51) Int. Cl.

| | | |
|---|---|---|
| C07C 331/20 | (2006.01) |
| A61K 31/26 | (2006.01) |
| A61P 17/00 | (2006.01) |
| A61K 9/00 | (2006.01) |
| A61K 31/145 | (2006.01) |
| A61K 45/06 | (2006.01) |
| A61K 47/34 | (2017.01) |
| A61K 31/198 | (2006.01) |
| A61K 9/06 | (2006.01) |

(52) U.S. Cl.
CPC .......... *C07C 331/20* (2013.01); *A61K 9/0014* (2013.01); *A61K 31/145* (2013.01); *A61K 31/198* (2013.01); *A61K 31/26* (2013.01); *A61K 45/06* (2013.01); *A61K 47/34* (2013.01); *A61K 9/06* (2013.01)

(58) Field of Classification Search
CPC .... C07C 331/20; A61K 31/26; A61K 31/145; A61K 31/198; A61K 47/34; A61K 9/0014; A61P 17/00
USPC ............... 514/514, 562, 563, 625, 663, 665; 558/17

See application file for complete search history.

(56) References Cited

U.S. PATENT DOCUMENTS

| | | |
|---|---|---|
| 2,905,701 A | 9/1959 | Nutting et al. |
| 3,108,040 A | 10/1963 | Folkers |
| 3,341,564 A * | 9/1967 | Potts ..................... C07C 331/16 548/530 |
| 3,725,030 A | 4/1973 | Newallis et al. |
| 3,740,435 A | 6/1973 | Newallis et al. |
| 3,969,087 A | 7/1976 | Saito et al. |
| 4,083,836 A | 4/1978 | Anjou et al. |
| 4,158,656 A | 6/1979 | Jones et al. |
| 4,191,752 A | 3/1980 | Kada et al. |
| 4,938,949 A | 7/1990 | Borch et al. |
| 5,114,969 A | 5/1992 | Chung et al. |
| 5,126,129 A | 6/1992 | Wiltrout et al. |
| 5,208,249 A | 5/1993 | Rowe et al. |
| 5,231,209 A | 7/1993 | Chung et al. |
| 5,290,578 A | 3/1994 | Passey et al. |
| 5,385,734 A | 1/1995 | Friedman |
| 5,411,986 A | 5/1995 | Cho et al. |
| 5,582,818 A | 12/1996 | Nakanishi et al. |
| 5,589,504 A | 12/1996 | Dannenberg et al. |
| 5,686,108 A | 11/1997 | Pusateri et al. |
| 5,725,895 A | 3/1998 | Fahey et al. |
| 5,882,646 A | 3/1999 | Pusateri et al. |
| 5,968,505 A | 10/1999 | Fahey et al. |
| 5,968,567 A | 10/1999 | Fahey et al. |
| 6,008,260 A | 12/1999 | Pezzuto et al. |

(Continued)

FOREIGN PATENT DOCUMENTS

| | | |
|---|---|---|
| CN | 101091705 | 12/2007 |
| EP | 0998943 | 5/2000 |

(Continued)

OTHER PUBLICATIONS

Talalay et al. Proc. Natl. Acad. Sci. 1988, 85, 8261-8265.*

(Continued)

*Primary Examiner* — Irina Neagu

(74) *Attorney, Agent, or Firm* — King & Partners, PLC

(57) ABSTRACT

The present invention relates to methods and compositions for the prevention and treatment of keratin-based skin diseases. In particular, the application describes compositions and methods of treating a patient suffering from skin blistering comprising the use of phase II enzyme inducers and/or activity modifiers.

3 Claims, No Drawings

(56) References Cited

U.S. PATENT DOCUMENTS

| | | | |
|---|---|---|---|
| 6,046,231 A | 4/2000 | Kosmeder, II et al. | |
| RE36,784 E | 7/2000 | Cho et al. | |
| 6,166,003 A | 12/2000 | Lam | |
| 6,172,250 B1 | 1/2001 | Seguin et al. | |
| 6,177,122 B1 | 1/2001 | Fahey et al. | |
| 6,242,018 B1 | 6/2001 | Fahey et al. | |
| 6,340,784 B1 | 1/2002 | Mithen et al. | |
| 6,348,220 B1 | 2/2002 | Ribnicky et al. | |
| 6,414,037 B1 | 7/2002 | Pezzuto et al. | |
| 6,436,450 B1 | 8/2002 | Omary et al. | |
| 6,455,554 B1 | 9/2002 | Dull et al. | |
| 6,465,512 B2 | 10/2002 | Nakamura et al. | |
| 6,492,399 B1 | 12/2002 | Dull et al. | |
| 6,524,594 B1 | 5/2003 | Santora et al. | |
| 6,680,062 B2 | 1/2004 | Muizzuddin et al. | |
| 6,737,441 B2 | 5/2004 | Fahey | |
| 6,824,796 B2 | 11/2004 | Pusateri et al. | |
| 6,878,751 B1 | 4/2005 | Donnelly et al. | |
| 6,991,811 B1 | 1/2006 | Brovelli et al. | |
| 7,303,770 B2 | 12/2007 | Fahey et al. | |
| 7,402,569 B2 | 7/2008 | Fahey | |
| 7,407,986 B2 | 8/2008 | Gao et al. | |
| 7,615,657 B2 | 11/2009 | Bathurst et al. | |
| 7,744,937 B2 | 6/2010 | West et al. | |
| 7,820,145 B2 | 10/2010 | Tamarkin et al. | |
| 7,879,822 B2 | 1/2011 | Dagan et al. | |
| 8,003,633 B1 | 8/2011 | Robertson et al. | |
| 8,008,281 B2 | 8/2011 | Prendergast et al. | |
| 8,039,511 B2 | 10/2011 | Cheng et al. | |
| 8,158,161 B2 | 4/2012 | Sussan et al. | |
| 8,168,655 B2 | 5/2012 | Gadek et al. | |
| 8,303,949 B2 | 11/2012 | Gao et al. | |
| 8,309,541 B1 | 11/2012 | Robertson et al. | |
| 8,410,037 B2 | 4/2013 | Molenda et al. | |
| 8,492,616 B2 | 7/2013 | Mero | |
| 8,510,127 B2 | 8/2013 | Hermann et al. | |
| 8,709,406 B2 | 4/2014 | Gao et al. | |
| 8,731,970 B2 | 5/2014 | Hermann et al. | |
| 8,772,251 B2 | 7/2014 | Morazzoni et al. | |
| 8,772,274 B1 | 7/2014 | Robertson et al. | |
| 8,835,721 B2 | 9/2014 | Mero | |
| 8,865,765 B2 | 10/2014 | Silver | |
| 8,865,772 B2 | 10/2014 | Silver | |
| 8,921,644 B2 | 12/2014 | Barten | |
| 8,933,119 B2 | 1/2015 | Silver | |
| 9,017,666 B2 | 4/2015 | Ashurst | |
| 9,096,505 B2 | 8/2015 | Robertson et al. | |
| 9,096,611 B2 | 8/2015 | Ren et al. | |
| 9,126,910 B2 | 9/2015 | Robertson et al. | |
| 9,126,911 B2 | 9/2015 | Robertson et al. | |
| 9,131,722 B2 | 9/2015 | Kim et al. | |
| 9,181,221 B2 | 11/2015 | Ren et al. | |
| 9,254,331 B2 | 2/2016 | Dubois et al. | |
| 9,308,192 B2 | 4/2016 | Coulombe et al. | |
| 9,315,505 B2 | 4/2016 | Ren et al. | |
| 9,359,349 B2 | 6/2016 | Ren et al. | |
| 9,393,225 B2 | 7/2016 | Beumer et al. | |
| 9,504,667 B2 | 11/2016 | Silver | |
| 9,532,969 B2 | 1/2017 | Silver | |
| 9,636,320 B2 | 5/2017 | Silver | |
| 9,642,827 B2 | 5/2017 | Silver | |
| 9,771,322 B2 | 9/2017 | Silver | |
| 9,828,337 B2 | 11/2017 | Silver | |
| 9,839,621 B2 | 12/2017 | Silver | |
| 9,931,314 B2 | 4/2018 | Silver | |
| 9,932,306 B2 | 4/2018 | Silver | |
| 9,949,943 B2 | 4/2018 | Silver | |
| 9,951,003 B2 | 4/2018 | Silver | |
| 9,951,004 B2 | 4/2018 | Silver | |
| 9,951,005 B2 | 4/2018 | Silver | |
| 9,962,361 B2 | 5/2018 | Silver | |
| 10,054,582 B2 | 8/2018 | Laughlin, II et al. | |
| 10,080,734 B2 | 9/2018 | Silver | |
| 10,111,852 B2 | 10/2018 | Silver | |
| 10,273,205 B2 | 4/2019 | Silver | |
| 10,287,246 B2 | 5/2019 | Silver | |
| 10,308,559 B2 | 6/2019 | Silver | |
| 10,308,599 B2* | 6/2019 | Silver | A61K 31/145 |
| 10,308,600 B2 | 6/2019 | Silver | |
| 10,335,387 B2 | 7/2019 | Silver | |
| 10,343,990 B2 | 7/2019 | Silver | |
| 10,363,236 B2* | 7/2019 | Silver | A61K 9/0014 |
| 10,640,464 B2* | 5/2020 | Silver | C07C 331/20 |
| 10,647,668 B2 | 5/2020 | Silver | |
| 10,654,799 B2 | 5/2020 | Silver | |
| 10,888,540 B2* | 1/2021 | Silver | A61K 9/0014 |
| 2002/0164381 A1 | 11/2002 | Shacknai et al. | |
| 2003/0185864 A1 | 10/2003 | Kobayashi et al. | |
| 2003/0198616 A1 | 10/2003 | Howard | |
| 2004/0156873 A1 | 8/2004 | Gupta | |
| 2005/0042182 A1 | 2/2005 | Arkin et al. | |
| 2005/0095261 A1 | 5/2005 | Popp | |
| 2005/0100621 A1 | 5/2005 | Popp et al. | |
| 2005/0118124 A1 | 6/2005 | Reinhart et al. | |
| 2005/0193448 A1 | 9/2005 | Gardner et al. | |
| 2006/0127996 A1 | 6/2006 | Fahey | |
| 2006/0160713 A1 | 7/2006 | Sekine et al. | |
| 2007/0041925 A1 | 2/2007 | Picano et al. | |
| 2008/0154210 A1 | 6/2008 | Jordan et al. | |
| 2008/0254150 A1 | 10/2008 | Rheins et al. | |
| 2008/0306148 A1 | 12/2008 | Robertson et al. | |
| 2008/0311192 A1 | 12/2008 | West et al. | |
| 2008/0311276 A1 | 12/2008 | West et al. | |
| 2009/0081138 A1 | 3/2009 | Ashurst | |
| 2009/0186853 A1 | 7/2009 | Yu et al. | |
| 2009/0324522 A1 | 12/2009 | Chevreau | |
| 2010/0124598 A1 | 5/2010 | West et al. | |
| 2011/0003747 A1 | 1/2011 | Coloumbe et al. | |
| 2011/0014137 A1 | 1/2011 | Talalay et al. | |
| 2011/0028548 A1 | 2/2011 | Fossel | |
| 2011/0195103 A1 | 8/2011 | Areas et al. | |
| 2012/0202878 A1 | 8/2012 | Silver | |
| 2013/0116203 A1 | 5/2013 | Rajski et al. | |
| 2014/0075590 A1 | 3/2014 | Van Den Bosch et al. | |
| 2015/0038579 A1 | 2/2015 | Silver | |
| 2015/0126600 A1 | 5/2015 | Silver | |
| 2016/0015676 A1 | 1/2016 | Silver | |
| 2016/0015677 A1 | 1/2016 | Silver | |
| 2016/0022624 A1 | 1/2016 | Silver | |
| 2016/0030379 A1 | 2/2016 | Silver | |
| 2016/0030380 A1 | 2/2016 | Silver | |
| 2016/0030381 A1 | 2/2016 | Silver | |
| 2016/0184363 A1 | 6/2016 | Badiavas et al. | |
| 2017/0037000 A1 | 2/2017 | Silver | |
| 2017/0037001 A1 | 2/2017 | Silver | |
| 2017/0258845 A1 | 9/2017 | Lim | |
| 2018/0344799 A1 | 12/2018 | Franklin | |
| 2019/0142788 A1 | 5/2019 | Hossain | |
| 2019/0292145 A1* | 9/2019 | Silver | A61K 31/145 |
| 2021/0244702 A1* | 8/2021 | Silver | A61P 17/00 |

FOREIGN PATENT DOCUMENTS

| | | |
|---|---|---|
| EP | 1 961 418 | 8/2008 |
| JP | 2000169321 | 6/2000 |
| JP | 2002284702 | 10/2002 |
| JP | 2008/193572 | 7/2006 |
| WO | WO 1994/005250 | 3/1994 |
| WO | WO 1994/019948 | 9/1994 |
| WO | WO 1997/007230 | 2/1997 |
| WO | WO 1997/026908 | 7/1997 |
| WO | WO 2005/016329 | 2/2005 |
| WO | WO 2006/065736 | 6/2006 |
| WO | WO 2007/056941 | 5/2007 |
| WO | WO 2008/070961 | 6/2008 |
| WO | WO 2009/088986 | 7/2009 |
| WO | WO 2010/140902 | 12/2010 |
| WO | WO 2012/010644 | 1/2012 |
| WO | WO 2012/064973 | 5/2012 |
| WO | WO 2013/003601 | 1/2013 |
| WO | WO 2016/172598 | 10/2016 |
| WO | WO 2017/122095 | 7/2017 |

(56) References Cited

FOREIGN PATENT DOCUMENTS

WO     WO 2017/218623     12/2017
WO     WO 2019/060719     3/2019

OTHER PUBLICATIONS

Zuang et al. Subgroup 2. Skin Irritation/Corrosion, in Cosmetics-European Commission, htttotl/ec.europa.eu/consumers/sectors/cosmetics/files/doc/antest/(5)chanter_3/2_skin_irritation_en.pdf., accessed Mar. 13, 2014.
Robert et al. New Engl. J. Med. 1999, 341 (24), 1817-1828.
Weber et al. The Journal of Emergency Medicine, 1999, 17 (2), 235-237.
Saint-Mezard et al. Eur. J. Dermatol. 2004, 14, 284-295.
PCT Written Opinion of the International Searching Authority for International Application No. PCT/US12/44660 dated Jul. 15, 2013.
PCT Written Opinion of the International Searching Authority for International Application No. PCT/US12/44593 dated Sep. 7, 2012.
PCT Written Opinion of the International Searching Authority for International Application No. PCT/US12/44628 dated Apr. 5, 2013.
PCT Written Opinion of the International Searching Authority for International Application No. PCT/US13/052307 dated Dec. 5, 2013.
Yehuda et al.. Potential skin anti-inflammatory effects of 4-methylthiobutylisothiocyanate (MTBI) isolated from rocket (Eruca Sativa) seeds, Biofactors 35(3), pp. 295-305, 2009. Abstract; p. 297, Fig. 1. https://www.researchgate.net/publication/24443311_Potential_skinantiinflammatory_effects_of_4-methylthiobutylisothiocyanate_MTBI_isolated_from_roceket_Eruca_saliva_seeds.
Valentine W. M et al.: "Covalent Cross-Linking of Erythrocyte Spectrin by Carbon Disulfide in Vivo," Toxicology and Applied Pharmacology, Academic Press, Amsterdam, NL, vol. 121, No. 1, Jul. 1, 1993 pp. 71-77.
Sundaram G. S. M. et al.: "Synthesis of Bioorthogonal and Crosslinking Amino Acids for Use in Peptide Synthesis," Amino Acids; The Forum for Amino Acid and Protein Research, Springer-Verlag, VI, vol. 39, No. 5, Apr. 22, 2010, pp. 1381-1384.
Mironov et al.: "Synthesis and Properties of New Chlorin and Bacteriochlorin Photosensitizers," Proceedings of SPIE; Photochemistry; Photodynamic Therapy and Other Modalities, vol. 2625, Jan. 31, 1996, pp. 23-32.
Allyl Isothiocyante Product Safety Data Sheet, sc-252361, pp. 1-14., print date Apr. 22, 2010.

Office Action for U.S. Appl. No. 13/342,516 dated May 22, 2013.
Office Action for U.S. Appl. No. 13/342,516 dated Mar. 18, 2014.
Office Action for U.S. Appl. No. 14/594,788 dated Sep. 30, 2015.
Office Action for U.S. Appl. No. 14/594,788 dated May 17, 2016.
Office Action for U.S. Appl. No. 14/880,408 dated Apr. 6, 2016.
Office Action for U.S. Appl. No. 14/880,408 dated Jul. 25, 2016.
Office Action for U.S. Appl. No. 14/880,408 dated Oct. 18, 2016.
Office Action for U.S. Appl. No. 14/880,418 dated Apr. 7, 2016.
Office Action for U.S. Appl. No. 14/880,418 dated Jul. 19, 2016.
Office Action for U.S. Appl. No. 14/880,418 dated Oct. 18, 2016.
Office Action for U.S. Appl. No. 14/880,426 dated Aug. 8, 2016.
Office Action for U.S. Appl. No. 14/880,426 dated Oct. 31, 2016.
Office Action for U.S. Appl. No. 13/348,821 dated Jan. 16, 2013.
Office Action for U.S. Appl. No. 13/348,821 dated Feb. 25, 2014.
Office Action for U.S. Appl. No. 14/519,462 dated Nov. 30, 2015.
Office Action for U.S. Appl. No. 14/519,462 dated Jul. 14, 2016.
Office Action for U.S. Appl. No. 14/868,897 dated Jun. 27, 2016.
Office Action for U.S. Appl. No. 14/868,929 dated Jul. 7, 2016.
Office Action for U.S. Appl. No. 14/868,959 dated Jul. 7, 2016.
Office Action for U.S. Appl. No. 13/952,236 dated Jun. 23, 2014.
Office Action for U.S. Appl. No. 14/519,510 dated Oct. 16, 2015.
Office Action for U.S. Appl. No. 14/519,510 dated Jun. 8, 2016.
Office Action for U.S. Appl. No. 14/867,585 dated Aug. 18, 2016.
Office Action for U.S. Appl. No. 14/867,626 dated Aug. 19, 2016.
Office Action for U.S. Appl. No. 13/351,616 dated Feb. 21, 2014.
Office Action for U.S. Appl. No. 13/351,616 dated Sep. 18, 2014.
Office Action for U.S. Appl. No. 13/351,616 dated Jan. 29, 2016.
Kricheldorf et al. Makromol. Chem. 1980, 181, 2571-2585.
Kricheldorf et al. Makromol. Chern. 1980, 181,2571-2585.
Office Action for U.S. Appl. No. 14/594,788 dated Jul. 10, 2017.
Office Action for U.S. Appl. No. 14/594,788 dated Jun. 20, 2017.
Office Action for U.S. Appl. No. 14/594,788 dated Apr. 12, 2017.
Office Action for U.S. Appl. No. 14/880,418 dated Sep. 20, 2017.
Office Action for U.S. Appl. No. 15/296,701 dated Jun. 21, 2017.
Office Action for U.S. Appl. No. 15/296,701 dated May 3, 2017.
Office Action for U.S. Appl. No. 15/297,304 dated Jun. 20, 2017.
Office Action for U.S. Appl. No. 15/297,304 dated May 3, 2017.
Office Action for U.S. Appl. No. 15/634,639 dated Aug. 25, 2017.
Office Action for U.S. Appl. No. 15/397,375 dated Sep. 25, 2017.
Office Action for U.S. Appl. No. 15/590,645 dated Jun. 8, 2017.
Office Action for U.S. Appl. No. 15/353,260 dated Aug. 9, 2017.
Office Action for U.S. Appl. No. 15/459,822 dated Oct. 6, 2017.
Office Action for U.S. Appl. No. 15/675,915 dated Nov. 1, 2017.

* cited by examiner

USE OF ISOTHIOCYANATE FUNCTIONAL SURFACTANTS AS NRF2 INDUCERS TO TREAT EPIDERMOLYSIS BULLOSA SIMPLEX AND RELATED DISEASES

CROSS-REFERENCE TO RELATED APPLICATIONS

This application is a continuation of U.S. application Ser. No. 16/506,119, entitled "USE OF ISOTHIOCYANATE FUNCTIONAL SURFACTANTS AS NRF2 INDUCERS TO TREAT EPIDERMOLYSIS BULLOSA SIMPLEX AND RELATED DISEASES," filed Jul. 9, 2019, now U.S. Pat. No. 10,640,464, which is a continuation of U.S. application Ser. No. 16/218,711, entitled "USE OF ISOTHIOCYANATE FUNCTIONAL SURFACTANTS AS NRF2 INDUCERS TO TREAT EPIDERMOLYSIS BULLOSA SIMPLEX AND RELATED DISEASES," filed Dec. 13, 2018, now U.S. Pat. No. 10,343,990, which is a continuation-in-part of U.S. application Ser. No. 15/675,915, entitled "USE OF ISOTHIOCYANATE FUNCTIONAL SURFACTANTS AS NRF2 INDUCERS TO TREAT EPIDERMOLYSIS BULLOSA SIMPLEX AND RELATED DISEASES," filed Aug. 14, 2017, which is a continuation-in-part of U.S. application Ser. No. 15/353,260, entitled "ISOTHIOCYANATE FUNCTIONAL SURFACTANTS, FORMULATIONS INCORPORATING THE SAME, AND ASSOCIATED METHODS OF USE," filed Nov. 16, 2016, now U.S. Pat. No. 9,962,361, which is a continuation-in-part of U.S. application Ser. No. 15/297,304, entitled "ISOTHIOCYANATE FUNCTIONAL SURFACTANT FORMULATION AND ASSOCIATED METHOD OF USE," filed Oct. 19, 2016, now U.S. Pat. No. 9,951,005, which is a continuation of U.S. application Ser. No. 14/594,788, filed Jan. 12, 2015, now U.S. Pat. No. 9,951,003, which is a continuation of U.S. application Ser. No. 13/342,516, filed Jan. 3, 2012, now U.S. Pat. No. 8,933,119, which claims the benefit of U.S. Provisional Application Ser. No. 61/502,067, filed Jun. 28, 2011, and U.S. Provisional Application Ser. No. 61/429,325, filed Jan. 3, 2011—all of which are hereby incorporated herein by reference in their entirety, including all references cited therein.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to isothiocyanate functional surfactants, formulations incorporating isothiocyanate functional surfactants, and associated methods of use—including, but not limited to, the use of isothiocyanate functional surfactants as nuclear factor (erythroid-derived 2)-like 2 (NFE2L2 or Nrf2) inducers and/or activity modifiers to treat epidermolysis bullosa simplex (i.e., a disorder resulting from mutations in the genes encoding keratin 5 or keratin 14) and related diseases.

2. Background Art

Natural, semi-sythentic, and/or synthetic compounds having one or more isothiocyanate functional groups and their associated uses have been known in the art for years and are the subject of a plurality of patents and publications, including, but not limited to: U.S. Pat. No. 8,772,251 entitled "Use Of Isothiocyanate Derivatives As Anti-Myeloma Agents," U.S. Pat. No. 7,303,770 entitled "Cancer Chemoprotective Food Products," U.S. Pat. No. 6,737,441 entitled "Treatment Of Helicobacter With Isothiocyanates," U.S. Pat. No. 6,340,784 entitled "Method For Selective Increase Of The Anti-carcinogenic Glucosinolates In Brassica Oleracea," U.S. Pat. No. 6,166,003 entitled "Heterocyclic Compounds For Cancer Chemoprevention," U.S. Pat. No. 5,411,986 entitled "Chemoprotective Isothiocyanates," U.S. Pat. No. 5,114,969 entitled "Method Of Inhibiting Lung Tumors, Arylalkyl Isothiocyanates, And Method Of Synthesizing Same," U.S. Pat. Application Publication No. US 2013/0116203 entitled "Isothiocynates And Glucosinolate Compounds And Anti-Tumor Compositions Containing Same," United States Patent Application Publication No. 2009/0081138 entitled "Cancer Chemoprotective Compositions And Natural Oils And Methods For Making Same," and United States Patent Application Publication No. 2006/0127996 entitled "Method Of Extraction Of Isothiocyanates Into Oil From Glucosinolate-Containing Plants And Method Of Producing Products With Oil Containing Isothiocyanates Extracted From Glucosinolate-Containing Plants," all of which are hereby incorporated herein by reference in their entirety— including all references cited therein.

U.S. Pat. No. 8,772,251 appears to disclose the use of glucomoringin (GMG) and its des-thio-glucoside (GMG-ITC) for the preparation of a medicament for the treatment of myeloma. The chemical structures of GMG and GMG-ITC are provided below:

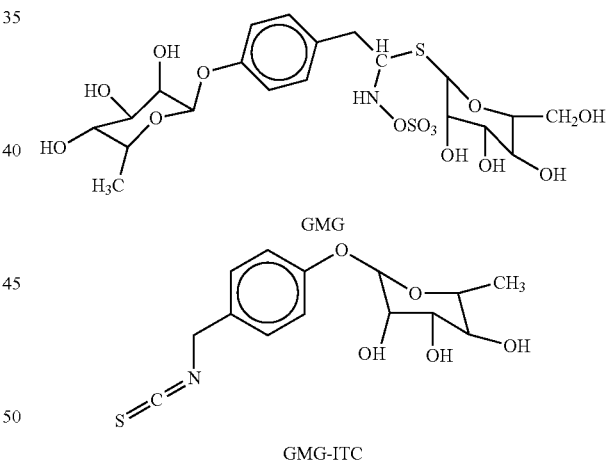

U.S. Pat. No. 7,303,770 appears to disclose vegetable sources that serve as chemoprotective agents. The chemoprotective agents disclosed are rich in glucosinolate (i.e., metabolic precursors to isothiocyanates). The vegetable sources are used to provide a dietary means of reducing the level of carcinogens in mammals.

U.S. Pat. No. 6,737,441 appears to disclose methods of preventing or inhibiting the growth of Helicobacter pylori through the use of a composition that comprises a glucosinolate, an isothiocyanate or a derivative or metabolite thereof. The '441 patent also appears to disclose methods of preventing or treating persistent chronic gastritis, ulcers and/or stomach cancer in subjects at risk for, or in need of treatment thereof.

U.S. Pat. No. 6,340,784 appears to disclose a method for producing Brassica oleracea with elevated anticarcinogenic glucosinolate derivatives. The elevated levels are obtained by crossing wild Brassica oleracea species with Brassica oleracea breeding lines, and subsequently selecting hybrids with levels of 4-methylsulfinylbutyl and/or 3-methylsulfinylpropyl glucosinolates elevated above that initially found in Brassica oleracea breeding lines. The invention also relates to edible brassica plants, such as broccoli plants, with elevated levels of 4-methylaulfinylbutyl glucosinolate and/or 3-methylsulfinylpropyl glucosinolates, and to seeds of such plants.

U.S. Pat. No. 6,166,003 appears to disclose a compound comprising a heterocyclic moiety, such as a thiophene, covalently attached to an alkylene isothiocyanate moiety. The compound is reportedly effective to prevent the occurrence or progression of cancer or a precancerous condition, and can be used for therapeutic or prophylactic purposes. The compound can be provided and administered in the form of a pharmaceutical composition, a cosmetic, a food additive, supplement, or the like. The '003 patent also discloses methods for synthesis and use of the chemopreventive compound.

U.S. Pat. No. 5,411,986 appears to disclose that sulforaphane has been isolated and identified as a major and very potent phase II enzyme inducer in broccoli (Brassica oleracea italica). Sulforaphane is disclosed as a monofunctional inducer, inducing phase II enzymes selectively without the induction of aryl hydrocarbon receptor-dependent cytochromes P-450 (phase I enzymes). The '986 patent discloses synthesizing analogues differing in the oxidation state of sulfur and the number of methylene groups, wherein their inducer potencies were measured. Sulforaphane was identified as the most potent of these analogues. Other analogues having different substituent groups in place of the methylsulfinyl group of sulforaphane were also synthesized and assessed. Of these, the most potent were 6-isothiocyanato-2-hexanone and exo-2-acetyl-6-isothiocyanatonorbornane.

U.S. Pat. No. 5,114,969 appears to disclose a method of inhibiting lung tumor multiplicity and/or incidence by treating mammals with relatively long chain arylalkyl isothiocyanates, especially effective with respect to tumors induced by exposure to tobacco-specific nitrosamine. Among the isothiocyanates disclosed are 4-phenylbutyl isothiocyanate, phenylpentyl isothiocyanate and phenylhexyl isothiocyanate, which are synthesized by adding hydrochloride of phenylbutylamine, phenylpentylamine, or phenylhexylamine in water to thiophosgene in an inert organic solvent.

United States Patent Application Publication No. 2013/0116203 appears to disclose glucosinolate and isothiocyanate compounds and related methods for synthesizing these compounds and analogs. In certain embodiments, these glucosinolate and isothiocyanate compounds are useful and chemopreventive and or chemotherapeutic agents. Examples include compounds of Formula I: R—N═C═S (I) wherein R is selected from the group consisting of dimethylpropyl, $C_3$-$C_{10}$ mono- or bicycloalkyl, $C_6$-$C_{10}$ mono- or bicycloakenyl, halobenzyl, alkyloxybenzyl, tetrahydronaphthalenyl, biphenyl-$C_1$-$C_6$-alkyl, phenoxybenzyl-$C_1$-$C_6$-alkyl, and pyridinyl-$C_1$-$C_6$-alkyl; N-acetyl cysteine conjugates thereof; and salts thereof.

United States Patent Application Publication No. 2009/0081138 appears to disclose chemoprotective compositions containing reduced oil-content extraction meals made from plants containing natural oils and glucosinolates. The oil content of the extraction meals may be reduced using batchwise or continuous supercritical fluid extractions. Also provided are glucosinolate-rich compositions containing purified glucosinolates isolated from plant materials. The glucosinolate-rich compositions may be made by reducing the oil content of a plant materials containing natural oils and glucosinolates and isolating the glucosinolates from the reduced oil-content plant materials using a membrane extraction. Natural oils containing isothiocyanates are also provided.

United States Patent Application Publication No. 2006/0127996 appears to disclose a method of extraction of isothiocyanates into oil from glucosinolate-containing plants and method of producing products with oil containing isothiocyanates extracted from glucosinolate-containing plants.

While the above-identified patents and publications do appear to disclose natural, semi-sythentic, and/or synthetic compounds having one or more isothiocyanate functional groups associated with a plurality of applications and/or uses, none of the above-identified patents and/or publications disclose isothiocyanate functional surfactants derived from natural and/or non-natural amino acids, including, but not limited to, lysine. Furthermore, none of the above-identified patents and/or publications disclose the use of isothiocyanate functional surfactants as Nrf2 inducers and/or activity modifiers to treat epidermolysis bullosa simplex (i.e., a disorder resulting from mutations in the genes encoding keratin 5 or keratin 14) and related diseases.

It is therefore an object of the present invention to provide novel isothiocyanate functional surfactants that will partially and/or fully remedy problems and/or complications associated with non-surfactant and/or non-lysine derived isothiocyanate functional compounds. It is therefore an additional object of the present invention to provide novel formulations incorporating isothiocyanate functional surfactants, and associated novel methods of use—including the use of isothiocyanate functional surfactants as Nrf2 inducers to treat epidermolysis bullosa simplex and related diseases.

These and other objects of the present invention will become apparent in light of the present specification, claims, chemical structures, chemical formulae, and drawings.

SUMMARY OF THE INVENTION

In one embodiment, the present invention is directed to an isothiocyanate functional surfactant, wherein said isothiocyanate functional surfactant comprises at least one isothiocyanate functional group associated with an aliphatic and/or aromatic carbon atom of the isothiocyanate functional surfactant.

The present invention is also directed to a lysine derivative, wherein the lysine derivative comprises an α-nitrogen and a ε-nitrogen, and wherein an alkyl and/or alkanoyl substituent comprising at least approximately 8 carbon atoms is associated with the α-nitrogen, and further wherein at least one isothiocyanate functional group is associated with the ε-nitrogen.

The present invention is further directed to a novel surfactant, wherein the protonated form of said surfactant is represented by the following chemical structure/representation:

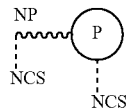

wherein the surfactant comprises a non-polar moiety (NP) and a polar moiety (P), and wherein at least one isothiocyanate functional group (NCS) is associated with the polar and/or non-polar moiety.

In another embodiment, the present invention is directed to a surfactant or a pharmaceutically acceptable salt thereof, wherein the protonated form of said surfactant is represented by the following chemical structure:

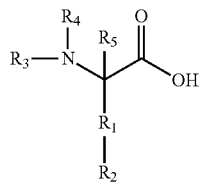

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

The present invention is also directed to a surfactant or a pharmaceutically acceptable salt thereof, wherein the protonated form of said surfactant is represented by the following chemical structure:

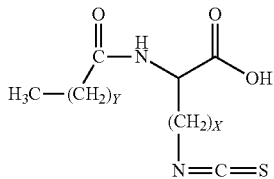

wherein X comprises an integer ranging from approximately 1 to approximately 25, and wherein Y comprises an integer ranging from approximately 6 to approximately 25.

In a preferred embodiment, the present invention is directed to a surfactant or a pharmaceutically acceptable salt thereof, wherein the protonated form of said surfactant is represented by the following chemical structure:

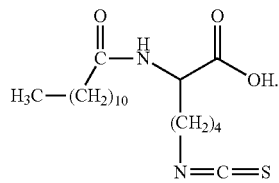

In another embodiment, the present invention is directed to a surfactant or a pharmaceutically acceptable salt thereof, wherein the surfactant is represented by the following chemical structure:

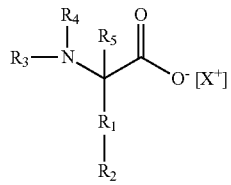

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4+$, wherein Z comprises, H, $R_6$, $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

The present invention is also directed to using one or more of the above-identified isothiocyanate functional surfactants as Nrf2 inducers and/or activity modifiers to treat epidermolysis bullosa simplex and related diseases.

DETAILED DESCRIPTION OF THE INVENTION

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

As is discussed in greater detail herein, the present invention is directed toward isothiocyanate functional surfactants and/or surfactant formulations. Preferably, these surfactants serve as Nrf2 inducers and/or activity modifiers to treat epidermolysis bullosa simplex and related diseases.

It will be understood that the term surfactant is derived from the contraction of the terms surface-active-agent and is defined herein as a molecule and/or group of molecules which are able to modify the interfacial properties of the liquids (aqueous and non-aqueous) in which they are present. The surfactant properties of these molecules reside in their amphiphilic character which stems from the fact that each surfactant molecule has both a hydrophilic moiety and a hydrophobic (or lipophilic) moiety, and that the extent of each of these moieties is balanced so that at concentrations at or below the critical micelle concentration (i.e., CMC) they generally concentrate at the air-liquid interface and materially decrease the interfacial tension. For example, sodium salts of saturated carboxylic acids are extremely soluble in water up to C8 length and are thus not generally regarded as true surfactants. They become less soluble in water from C9 up to C18 length, the domain of effective surfactants for this class of compounds. The carboxylic acids (fatty acids) can be either saturated or unsaturated starting from C16 chain lengths.

Without being bound by any one particular theory, it is believed that the isothiocyanate functional surfactants disclosed herein serve as Nrf2 inducers and/or activity modifiers. It is also believed that the isothiocyanate functional surfactants disclosed herein facilitate elevating phase II enzymes (e.g., HAD(P)H quinine oxidoreductase) which are believed to, among other things regulate inflammatory responses within the body, as well as detoxify potential and active mutagens. Relevant experimental data regarding the foregoing can be found in, for example, International Application No. PCT/US2008/008694, U.S. Pat. No. 9,308,192, and U.S. Patent Application Publication No. 2011/0003747, all of which are entitled "USE OF NRF2 INDUCERS TO TREAT EPIDERMOLYSIS BULLOSA SIMPLEX AND RELATED DISEASES,"—and all of which are hereby incorporated herein by reference in their entirety, including all references cited therein.

In accordance with the present invention, the isothiocyanate functional surfactants may be used as a topical leave-on product in which one or more surfactants remain on the skin and are not immediately and/or ever rinsed off away from the skin. Alternatively, the isothiocyanate functional surfactants of the present invention may be used as a topical wash in an apply-and-rinse fashion. For either case, it is preferred that the isothiocyanate functional surfactants be generally mild to human skin (e.g., non-irritating or low-irritating). In particular, anionic N-alkanoyl surfactants derived from amino acids are especially preferred because, while not completely predictable, they have a tendency to be mild. The methods of preparation detailed in this invention employ but are not limited to amino acids that possess at least two amine functionalities, at least one of which is converted to an N-alkanoyl functionality, and at least one of which is converted into isothiocyanate functionality. The amino acids include but are not limited to the α-amino acids lysine, ornithine, 2,4-diaminobutanoic acid, 2,3-diaminopropionic acid 2,7-diaminoheptanoic acid, and 2,8-diaminopropionic acid. Additionally, amino acids other than α-amino acids may be employed, such as β-amino acids, etcetera. It will be understood that amino acid derived surfactants are preferred due to their mild nature, but any one of a number of other surfactants are likewise contemplated for use in accordance with the present invention.

The methods for preparing isothiocyanate functional surfactants and/or their precursors can involve, but are not limited to, conversion of an amine functionality to an isothiocyanate functionality. The methods of conversion of amine functionalities to isothiocyanate functionalities may comprise, but are not limited to: (1) reaction with carbon disulfide to yield an intermediate dithiocarbamate, followed by reaction with ethylchloroformate or its functional equivalent such as bis(trichloromethyl)-carbonate, trichloromethyl chloroformate, or phosgene; (2) reaction with thiophosgene; (3) reaction with 1,1'-thiocarbonyldiimidizole; (4) reaction with phenylthiochloroformate; (5) reaction with ammonium or alkali metal thiocyanate to prepare an intermediate thiourea followed by cleaving to the isothiocyanate via heating; and (6) reaction with an isothiocyanato acyl halide [SCN—$(CH_2)_n$—CO—Cl]. The resulting isothiocyanate functional surfactant, depending on the method of preparation, can be isolated as a pure material or as a mixture with other surfactants. The resulting isothiocyanate functional surfactant, depending on the method of preparation, can be isolated and used directly in nonionic form, anionic form, cationic form, zwitterionic (amphoteric) form, or in a neutral surfactant-precursor form in combination with a base such as sodium hydroxide or triethanol amine if the neutral surfactant-precursor form possesses a protonated carboxylic acid group such that reaction (deprotonation) with the base converts the neutral surfactant-precursor form to an anionic surfactant, or in neutral surfactant-precursor form in combination with an acid if the neutral surfactant-precursor form possess amine functionality such that reaction (protonation) with the acid converts the neutral surfactant-precursor form to a cationic surfactant.

In accordance with the present invention the isothiocyanate functional surfactants can be applied and/or associated with a human using any one of a number of techniques including, but not limited to, spraying, dripping, dabbing, rubbing, blotting, dipping, and any combination thereof.

In certain preferred embodiments of the present invention, the isothiocyanate functional surfactants are removed from the affected area after a period of time. Such a period comprises, but is not limited to, seconds (e.g., 1 second, 2 seconds, 5 seconds, 10 seconds, 15 seconds, 20 seconds, 30 seconds, 45 seconds, and 60 seconds), minutes (e.g., 1 minute, 2 minutes, 5 minutes, 10 minutes, 15 minutes, 20 minutes, 30 minutes, 45 minutes, and 60 minutes), hours (e.g., 1 hour, 2 hours, 5 hours, 10 hours, 15 hours, 20 hours, 30 hours, 45 hours, and 60 hours), days (e.g., 1 day, 2 days, 3 days, 4 days, 5 days, 6 days, 7 days, 10 days, 14 days, 21 days, 30 days), etcetera. It will be understood that the step of removing preferably occurs via rinsing, wiping, and/or extracting—just to name a few.

Depending upon the subject and/or the severity of the medical condition, multiple applications may be necessary. As such, the steps of applying and/or removing the isothiocyanate functional surfactants may be repeated once or a plurality of times.

In one embodiment, the present invention is directed to an isothiocyanate functional surfactant, wherein said isothiocyanate functional surfactant comprises at least one isothiocyanate functional group associated with an aliphatic and/or aromatic carbon atom of the isothiocyanate functional surfactant.

The present invention is also directed to a lysine derivative, wherein the lysine derivative comprises an α-nitrogen and a ε-nitrogen, and wherein an alkyl and/or alkanoyl substituent comprising at least approximately 8 carbon atoms is associated with the α-nitrogen, and further wherein at least one isothiocyanate functional group is associated with the ε-nitrogen.

The present invention is further directed to a novel surfactant, wherein the protonated form of said surfactant is represented by the following chemical structure/representation:

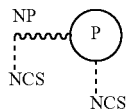

wherein the surfactant comprises a non-polar moiety (NP) and a polar moiety (P), and wherein at least one isothiocyanate functional group (NCS) is associated with the polar and/or non-polar moiety.

In another embodiment, the present invention is directed to a surfactant or a pharmaceutically acceptable salt thereof, wherein the protonated form of said surfactant is represented by the following chemical structure:

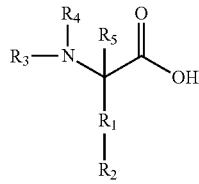

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

The present invention is also directed to a surfactant or a pharmaceutically acceptable salt thereof, wherein the protonated form of said surfactant is represented by the following chemical structure:

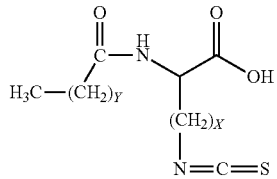

wherein X comprises an integer ranging from approximately 1 to approximately 25, and wherein Y comprises an integer ranging from approximately 6 to approximately 25.

More preferably, the surfactant is represented by one or more of the following chemical structures:

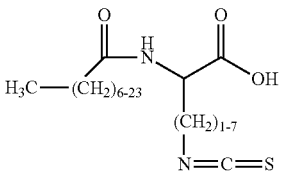

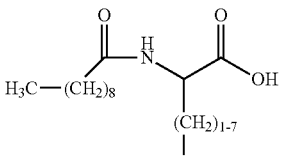

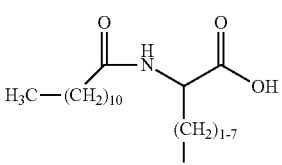

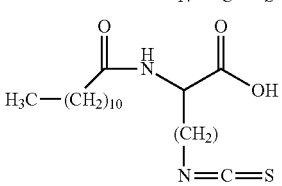

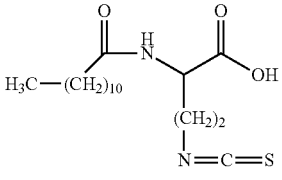

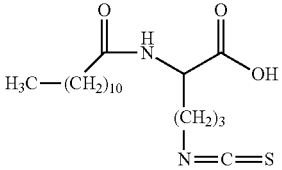

-continued
In another embodiment, the present invention is directed to a surfactant or a pharmaceutically acceptable salt thereof, wherein the protonated form of the surfactant is represented by the following chemical structure:

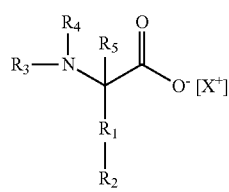

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4+$, wherein Z comprises, H, $R_6$, $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

In accordance with the present invention, the isothiocyanate functional surfactant may be associated with an additional surfactant, wherein the additional surfactant is selected from at least one of the group comprising a nonionic surfactant, an anionic surfactant, a cationic surfactant, a zwitterionic surfactant, and combinations thereof.

Non-limiting examples of preferred anionic surfactants include taurates; isethionates; alkyl and alkyl ether sulfates; succinamates; alkyl sulfonates, alkylaryl sulfonates; olefin sulfonates; alkoxy alkane sulfonates; sodium and potassium salts of fatty acids derived from natural plant or animal sources or synthetically prepared; sodium, potassium, ammonium, and alkylated ammonium salts of alkylated and acylated amino acids and peptides; alkylated sulfoacetates; alkylated sulfosuccinates; acylglyceride sulfonates; alkoxyether sulfonates; phosphoric acid esters; phospholipids; and combinations thereof. Specific anionic surfactants contemplated for use include, but are by no means limited to, ammonium cocoyl isethionate, sodium cocoyl isethionate, sodium lauroyl isethionate, sodium stearoyl isethionate, sodium lauroyl sarcosinate, sodium cocoyl sarcosinate, sodium lauryl sarcosinate, disodium laureth sulfosuccinate, sodium lauryl sulfoacetate, sodium cocoyl glutamate, TEA-cocoyl glutamate, TEA cocoyl alaninate, sodium cocoyl taurate, potassium cetyl phosphate.

Non-limiting examples of preferred cationic surfactants include alkylated quaternary ammonium salts $R_4NX$; alkylated amino-amides $(RCONH-(CH_2)_n)NR_3X$; alkylimidazolines; alkoxylated amines; and combinations thereof. Specific examples of anionic surfactants contemplated for use include, but are by no means limited to, cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, distearyl methyl ammonium chloride, distearyl methyl ammonium bromide, ditallow dimethyl ammonium chloride, ditallow dimethyl ammonium sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-imonium chloride phosphate, stearamidopropyl ethyldimonium ethosulfate, stearimidopropyldimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, ditallowyl oxyethyl dimethyl ammonium chloride, behenamidopropyl PG dimonium chloride, dilauryl dimethyl ammonium chloride, distearly dimethyl ammonium chloride, dimyristyl dimethyl ammonium chloride, dipalmityl dimethyl ammonium chloride, distearyl dimethyl ammonium chloride, stearamidoproyl PG-dimonium chloride phosphate, stearamidopropyl ethyldiammonium ethosulfate, stearamidopropyl dimethyl (myristyl acetate) ammonium chloride, stearimidopropyl dimethyl cetaryl ammonium tosylate, stearamido propyl dimethyl ammonium chloride, stearamidopropyl dimethyl ammonium lactate.

Non-limiting examples of preferred non-ionic surfactants include alcohols, alkanolamides, amine oxides, esters (including glycerides, ethoxylated glycerides, polyglyceryl esters, sorbitan esters, carbohydrate esters, ethoxylated carboxylic acids, phosphoric acid triesters), ethers (including ethoxylated alcohols, alkyl glucosides, ethoxylated polypropylene oxide ethers, alkylated polyethylene oxides, alkylated polypropylene oxides, alkylated PEG/PPO copolymers), and silicone copolyols. Specific examples of non-ionic surfactants contemplated for use include, but are by no means limited to, cetearyl alcohol, ceteareth-20, nonoxynol-9, C12-15 pareth-9, POE(4) lauryl ether, cocamide DEA, glycol distearate, glyceryl stearate, PEG-100 stearate, sorbitan stearate, PEG-8 laurate, polyglyceryl-10 trilaurate, lauryl glucoside, octylphenoxy-polyethoxyethanol, PEG-4 laurate, polyglyceryl diisostearate, polysorbate-60, PEG-200 isostearyl palmitate, sorbitan monooleate, polysorbate-80.

Non-limiting examples of preferred zwitterionic or amphoteric surfactants include betaines; sultaines; hydroxysultaines, amido betaines, amidosulfo betaines; and combinations thereof. Specific examples of amphoteric surfactants contemplated for use include, but are by no means limited to, cocoamidopropyl sultaine, cocoamidopropyl hydroxyl sultaine, cocoamidopropylbetaine, coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl (2-bishydroxy) carboxymethyl betaine, stearyl bis-(2-hydroxyethyl) carboxymethyl betaine, oelyl dimethyl gamma-carboxypropyl betaine, lauryl bis-(2-hydroxypropyl)alpha carboxymethyl betaine, coco dimethyl sulfopropyl betaine, stearyl dimethyl sulfopropyl betaine, lauryl dimethyl sulfoethyl betaine, lauryl bis(2-hydroxyethyl) sulfopropyl betaine, oleyl betaine, cocamidopropyl betaine.

In further accordance with the present invention, the isothiocyanate functional surfactant may be incorporated into a formulation comprising one or more solvents. Preferably, the solvent comprises a hydrocarbon and/or silicone oil that is generally non-hygroscopic and/or generally hydrophobic. Suitable examples, include, silicone based solvents and/or fluids, mineral oil, vegetable oils, squalene (i.e., 2,6,10,15,19,23-hexamethyltetracosane)—just to name a few.

The invention is further described by the following examples.

EXAMPLE I

Preparation of a Mixture of $N_\alpha$-lauroyl-$N_\varepsilon$-isothiocyanato-L-Lysine with $N_\alpha,N_\varepsilon$-bis-lauroyl-L-lysine A 1 liter beaker equipped with an overhead mechanical stainless steel paddle stirrer was charged with 100 mL of 1 M NaOH (0.100 mol). Stirring was begun and the beaker cooled to −5° C. to −10° C. using a salt/ice bath. Next, 23.4 g (0.100 mol) of $N_\varepsilon$-benzylidene-L-lysine (prepared via the method of Bezas, B and Zervas, L., JACS, 83, 1961, 719-722) was added. Immediately afterward and while keeping the solution cold, 140 mL (0.140 mol) of precooled (in a salt/ice bath) 1 M NaOH and 26.1 mL of lauroyl chloride was added in two equal portions over a period of 6 minutes. The mixture was stirred for 10 more minutes at −5 to −10° C., then the ice bath was removed and the reaction mixture allowed to stir for another 1 hour while warming to room temperature. Next, the reaction mixture was cooled using a salt/ice bath and then sufficient concentrated HCl was added to adjust the pH to 7.5-7.8. With the pH at 7.8-7.8 and with continued cooling and stirring, 4.6 mL (60% of stoichiometric, 0.068 mol) of thiophosgene was added dropwise via an additional funnel over the period of 1 hour. During this time, sufficient 1 M NaOH was added to maintain a pH range between 7.5-7.8. After the thiophosgene addition was complete, additional 1 M NaOH was added as necessary until the pH stabilized in 7.5-7.8 range. Next, sufficient 30% NaOH was added to adjust the pH to approximately 8.5. Next, 12 mL (0.051 mol) of lauroyl chloride was rapidly added, followed by sufficient 1 M NaOH to keep the pH in the range of 8.00-8.50. Next, sufficient concentrated HCl was added to adjust the pH to 1.5. The reaction mixture was filtered via vacuum filtration, and the precipitate washed with dilute HCl (pH=2). The product, a white moist solid, was dried in vacuo while heating to 60° C. 45.19 g of white solid product was recovered, a mixture of predominantly $N_\alpha$-lauroyl-$N_\varepsilon$-isothiocyanato-L-lysine and $N_\alpha,N_\varepsilon$-bis-lauroyl-L-lysine (determined via LC-MS analysis). Both compounds in this mixture can be simultaneously converted into anionic (carboxylate) surfactants via reaction with aqueous NaOH to yield a clear aqueous solution of the surfactants.

EXAMPLE II

Preparation of Pure $N_\alpha$-lauroyl-$N_\varepsilon$-isothiocyanato-L-Lysine

Step 1: Preparation of $N_\alpha$-lauroyl-$N_\varepsilon$-carbobenzoxy-L-Lysine 60.0 g of $N_\varepsilon$-cbz-L-Lysine (cbz is carbobenzoxy) purchased from Atomole Scientific Company, LTD was added to a three-liter beaker along with 1200 mL of RO water and the mixture was stirred. Next, 39 mL of 30% aqueous NaOH was added, resulting in dissolution of the $N_\varepsilon$-cbz-L-Lysine. The resulting solution was cooled in an ice bath and then 52.5 mL of lauroyl chloride was added. The ice bath was removed 30 minutes later, and stirring continued for an additional six hours, at which time 18 mL of concentrated hydrochloric acid was added. The reaction mixture was then filtered via vacuum filtration, the white solid product washed with 1 M aqueous HCl, and then the solid product was dried in vacuo while heated to approximately 85° C. 96.5 g of dry white solid product was obtained. The product can be further purified by dissolving it in methanol, filtering off any insoluble precipitate, and removing the methanol in vacuo to recover a white solid product (mp 99.5-103.0° C.)

Step 2: Preparation of $N_\alpha$-Lauroyl-$N_\varepsilon$-Ammonium Chloride-L-Lysine 10.0 g of $N_\alpha$-lauroyl-$N_\varepsilon$-carbobenzoxy-L-Lysine was weighed into a one liter Erlenmeyer flask equipped with a magnetic stir bar. 150 mL of concentrated hydrochloric acid was added and the solution was stirred and heated in an oil bath to 104° C., then allowed to cool with the oil bath back to room temperature. The solution was then cooled to 9° C. for approximately four hours, during which time a large mass of white precipitate formed. The reaction mixture was filtered in vacuo and rinsed with a small amount of cold 1 M HCl. The white solid reaction product was then dried in vacuo while being heated to 78° C., yielding 7.89 g of white solid product (mp 191-193° C.).

Step 3: Preparation of $N_\alpha$-lauroyl-$N_\varepsilon$-isothiocyanato-L-Lysine 0.46 mL of thiophosgene was added to 30 mL of dichloromethane in a 125 mL Erlenmeyer flask equipped with a magnetic stir bar. To this solution was drop wise added over 15 minutes a solution consisting of 2.00 g $N_\alpha$-lauroyl-$N_\varepsilon$-ammonium chloride-L-Lysine, 10 mL RO water, and 2.7 mL 20% aqueous NaOH. Stirring was continued for an additional 30 minutes, after which sufficient concentrated hydrochloric acid was added to lower the pH to 1 as indicated by testing with pHydrion paper. The reaction solution was then transferred into a separatory funnel and the bottom turbid dichloromethane layer was isolated and dried with anhydrous magnesium sulfate and gravity filtered. To the filtrate was added 50 mL of hexanes. The solution was then concentrated via removal of 34 mL of solvent via trap-to-trap distillation and then placed in a −19° C. freezer. A mass of white precipitate formed after a few hours and was isolated via vacuum filtration and then dried in vacuo for 2 hours. 1.130 g of a slightly off white solid powder product was obtained [mp 37.0-39.0° C.; IR (cm$^{-1}$), 3301 sb, 2923 s, 2852 s, 2184 m, 2099 s, 1721 s, 1650 s, 1531 s, 1456 m, 1416 w, 1347 m, 1216 m, 1136 w]

EXAMPLE III

Preparation of a Two-Part Formulation

A two-part formulation for topical application to the skin was prepared as follows:

Part I: A 25% by mass mixture of $N_\alpha$-lauroyl-$N_\epsilon$-isothiocyanato-L-Lysine in Dow Corning DC344 fluid (a mixture of octamethyl-cyclotetrasiloxane and decamethyl-cyclopentasiloxane) was prepared in a mortar and pestle to produce a paste that was loaded into a 5 ml plastic disposable syringe. A syringe needle was not employed. Rather, the dispensing end of the syringe was capped except for when dispensing without a syringe needle into the palm of a hand occurred.

Part II: Part II consisted of Cetaphil Moisturizing Lotion to which additional triethanol amine (TEA) was added such that the concentration of the additional triethanol amine was 0.006 g triethanol amine per gram of lotion, raising the pH of the Cetaphil Lotion from 7.74 to 8.77.

Preferred Instructions for Application of Formulation to the Skin: A 0.2 mL portion of the $N_\alpha$-lauroyl-$N_\epsilon$-isothiocyanato-L-Lysine/DC344 mixture is dispensed from the syringe into the palm of a hand (approximately 0.13 g of the mixture). Next, two full squirts of the Cetaphil/TEA lotion is dispensed on top of the $N_\alpha$-lauroyl-$N_\epsilon$-isothiocyanato-L-Lysine/DC344 mixture (approximately 2.8 g of the lotion). Next, using the index finger of the other hand, the components are mixed thoroughly for 30 seconds, during which time the water insoluble $N_\alpha$-lauroyl-$N_\epsilon$-isothiocyanato-L-Lysine surfactant-precursor is deprotonated to yield the water-soluble anionic (carboxylate) surfactant and yield a homogenous smooth white lotion (this reduces the pH to 7.4). This mixture is then applied to the afflicted areas by gently rubbing it on as one would apply any moisturizing lotion.

EXAMPLE IV

Preparation of a One-Part Formulation

A one-part formulation for topical application to the skin was prepared as follows:

First, 0.00025% (by wt.; 5.0 micromolar) of Sodium $N_\alpha$-lauroyl-$N_\epsilon$-isothiocyanate-L-Lysinate, the sodium salt of the material provided in step three of Example II, was associated with (QS to achieve 100%) 2,6,10,15,19,23-Hexamethyltetracosane (commercially available from Sigma-Aldrich). It will be understood that the concentration of Sodium $N_\alpha$-lauroyl-$N_\epsilon$-isothiocyanate-L-Lysinate may range from approximately 0.000001% to approximately 50%. Non-limiting examples of additional concentrations include 0.0005%, 0.005%, 0.005%, 0.005%, 0.05%, 0.5%, 5%—just to name a few.

Preferred Instructions for Application of the One-Part Formulation to the skin: A 0.1-1.0 mL portion of the one-part formulation is dispensed from a container into the palm of a hand for subsequent administration to an affected area and/or is dispensed directly onto an affected area by gently rubbing it on as one would apply a moisturizing lotion.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and Desired to be Secured by Letters Patent of the United States is:

1. A method for treating a patient having dowling-meara type epidermolysis bullosa simplex, comprising the step of administering to the patient an isothiocyanate functional surfactant, wherein the protonated form of the isothiocyanate functional surfactant is represented by the following chemical structure:

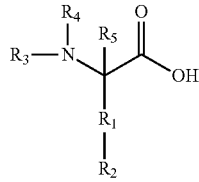

wherein $R_1$ is selected from the group consisting of an alkyl, aryl, and alkenyl group containing 1 to 25 carbon atom(s); wherein $R_2$ is selected from the group consisting of NCS; and wherein $R_3$-$R_5$ are each independently selected from the group consisting of H; OH; and an alkyl, aryl, alkaryl, aralkyl, alkoxy, alkanoyl, aroyl, and alkenyl group containing 1 to 25 carbon atom(s) with the proviso that at least one of $R_3$-$R_5$ is selected from the group consisting of an alkyl, aryl, alkaryl, aralkyl, alkoxy, alkanoyl, aroyl, and alkenyl, group containing 8 to 25 carbon atoms.

2. The method according to claim 1, wherein the protonated form of the isothiocyanate functional surfactant is represented by the following chemical structure:

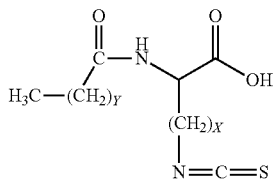

wherein X is an integer ranging from 1 to 25, and wherein Y is an integer ranging from 6 to 25.

3. The method according to claim 1, wherein the protonated form of the isothiocyanate functional surfactant is represented by the following chemical structure:

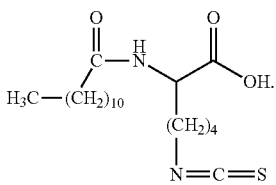

* * * * *